United States Patent [19]

Gess

[11] 4,409,690
[45] Oct. 18, 1983

[54] INTRAOCULAR LENSES

[76] Inventor: Lowell A. Gess, 111 15th Ave., East, Alexandria, Minn. 56308

[21] Appl. No.: 305,384

[22] Filed: Sep. 24, 1981

[51] Int. Cl.$^3$ .......................... A61F 1/16; A61F 1/24
[52] U.S. Cl. ........................................... 3/13; 128/335
[58] Field of Search ................. 3/13; 128/335, 334 R, 128/DIG. 26

[56] References Cited

U.S. PATENT DOCUMENTS

| | | | |
|---|---|---|---|
| 4,092,743 | 6/1978 | Kelman | 3/13 |
| 4,174,543 | 11/1979 | Kelman | 3/13 |
| 4,198,714 | 4/1980 | Jensen | 3/13 |
| 4,254,510 | 3/1981 | Tennant | 3/13 |
| 4,275,736 | 6/1981 | Chodorow et al. | 128/335 |
| 4,277,852 | 7/1981 | Poler | 3/13 |
| 4,298,994 | 11/1981 | Clayman | 3/13 |

FOREIGN PATENT DOCUMENTS 563174  7/1977  U.S.S.R. .................................... 3/13

Primary Examiner—Ronald L. Frinks
Attorney, Agent, or Firm—Harvey B. Jacobson

[57] ABSTRACT

Intraocular lenses for implantation into either of the anterior or posterior chambers of a human eye comprise an improved superior limb fixation element which enables lens insertion to be accomplished easier and more exact with assured fixation in the desired chamber over prior art intraocular lenses. The novel superior limb projects laterally from the peripheral edge of the plano-convex lens body and is structured to hold a suture for permanent fixation of the lens within the desired chamber. The suture holding structure of the superior limb comprises a widened and flattened head placed on the distal end of the superior limb and includes a hole or slit placed through the flattened head portion for holding the suture, the flattened head of the superior limb further including a depression surrounding the suture hole or slit to enable the accommodation and guiding of forceps to thread the suture through the slit or hole. Preferably, the plano-convex lens body as well as the laterally projecting superior and lower limb fixation elements are of a one-piece molded suitable physiologically insert plastic, but may also be formed together from separate elements.

5 Claims, 16 Drawing Figures

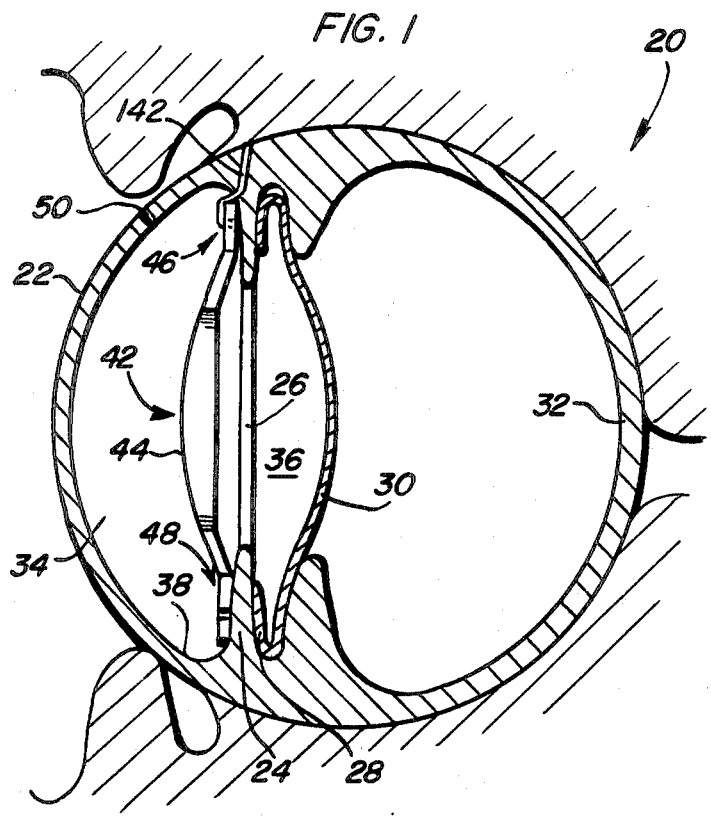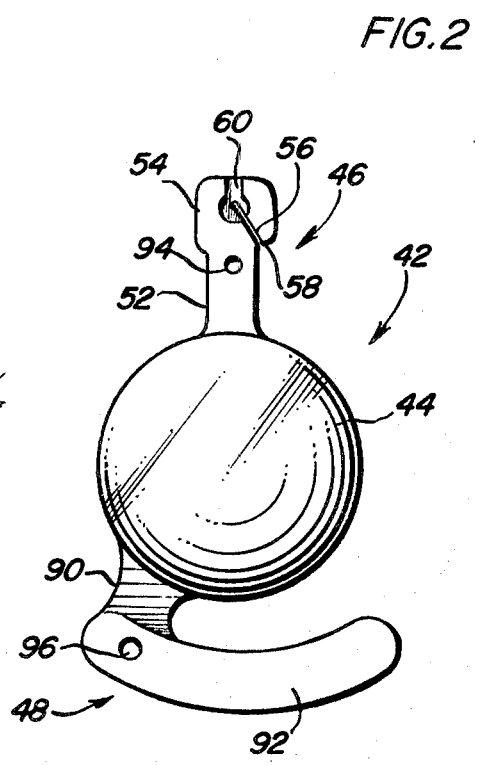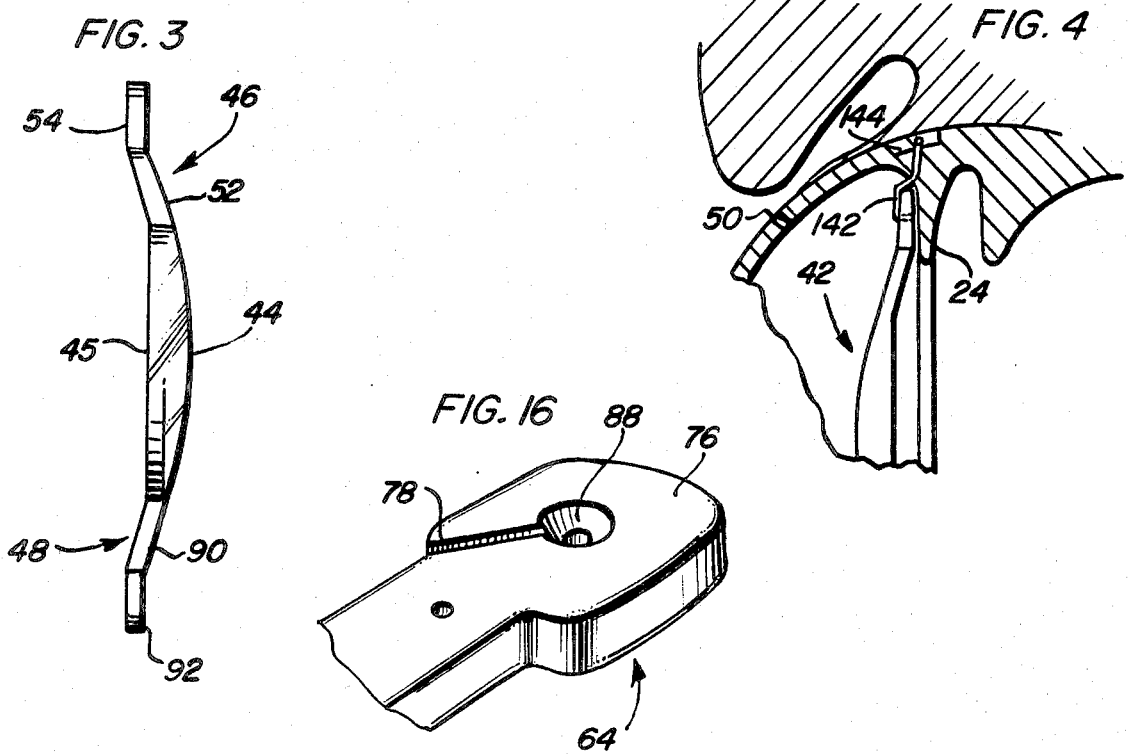

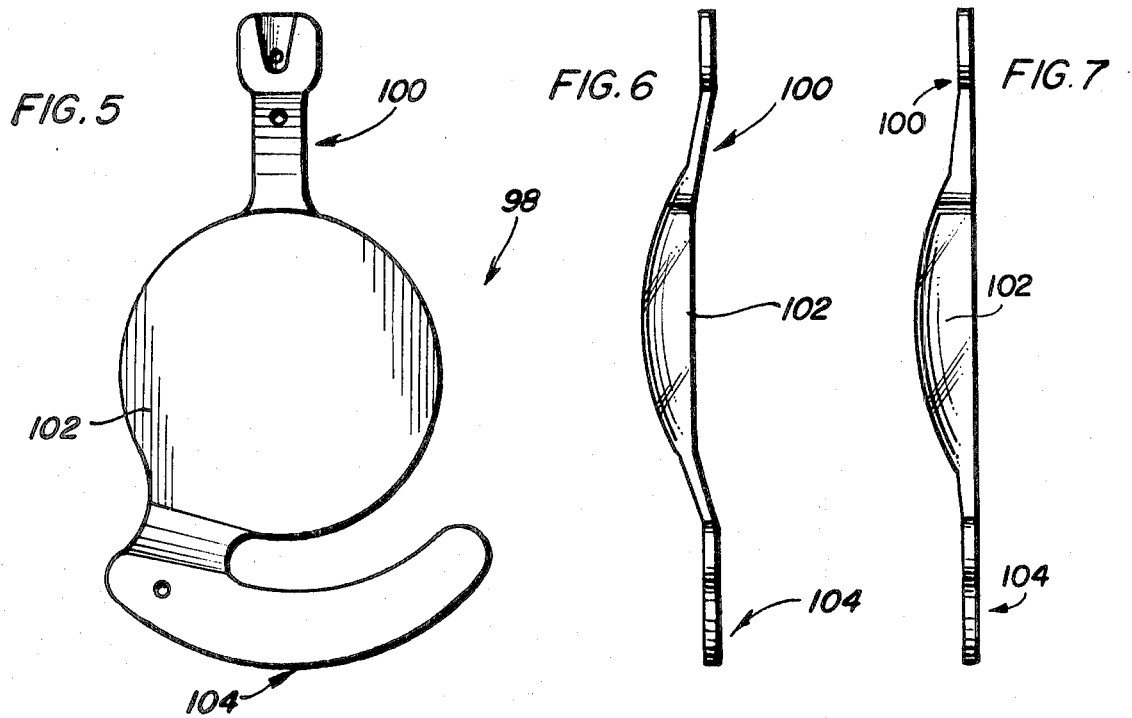
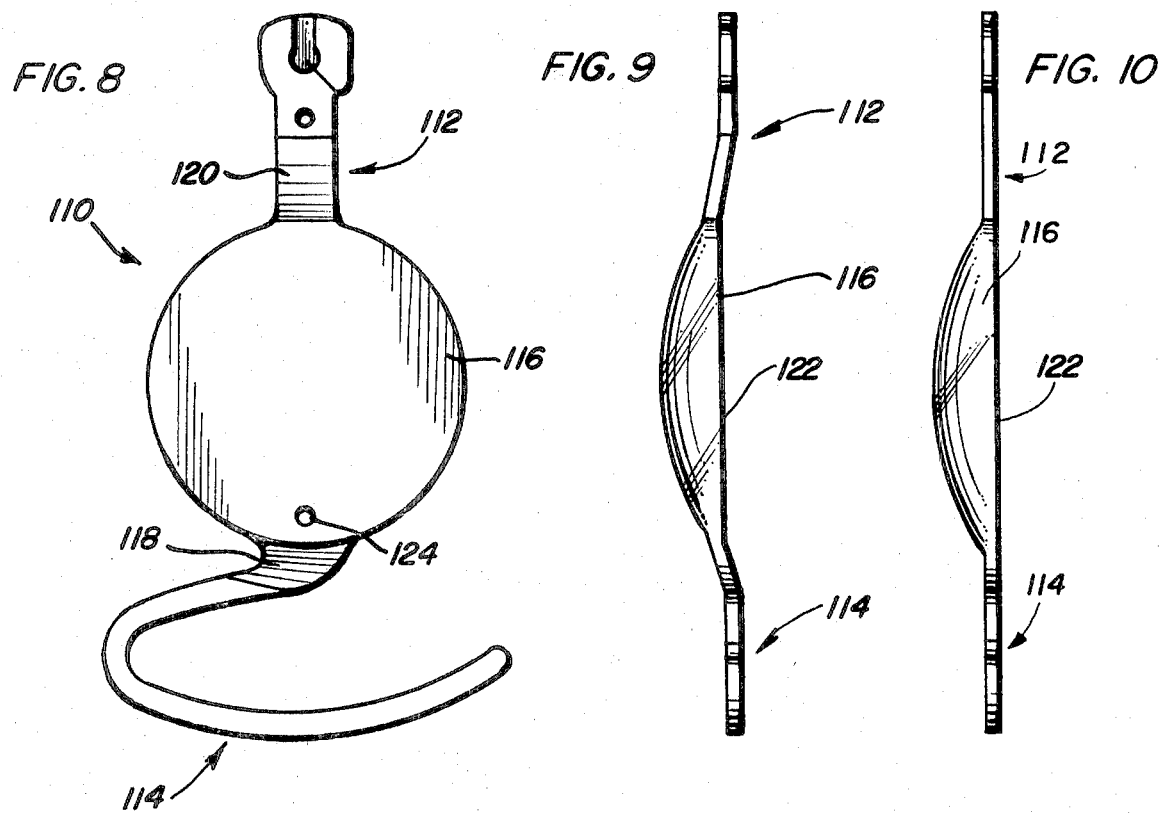

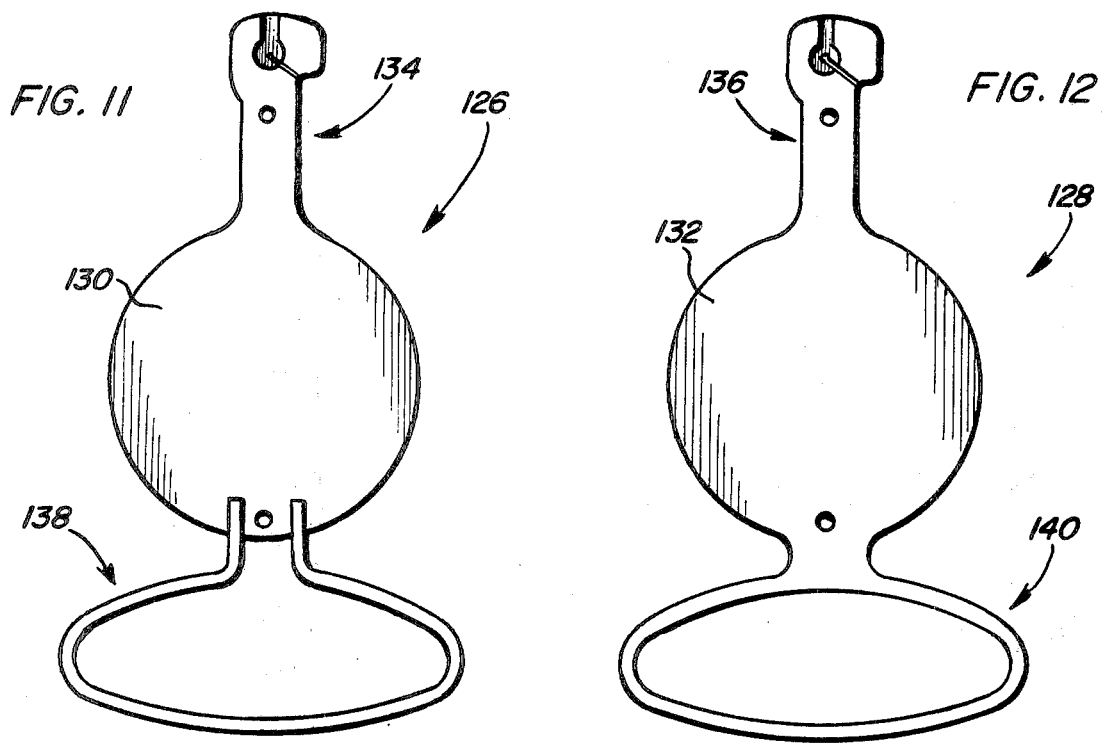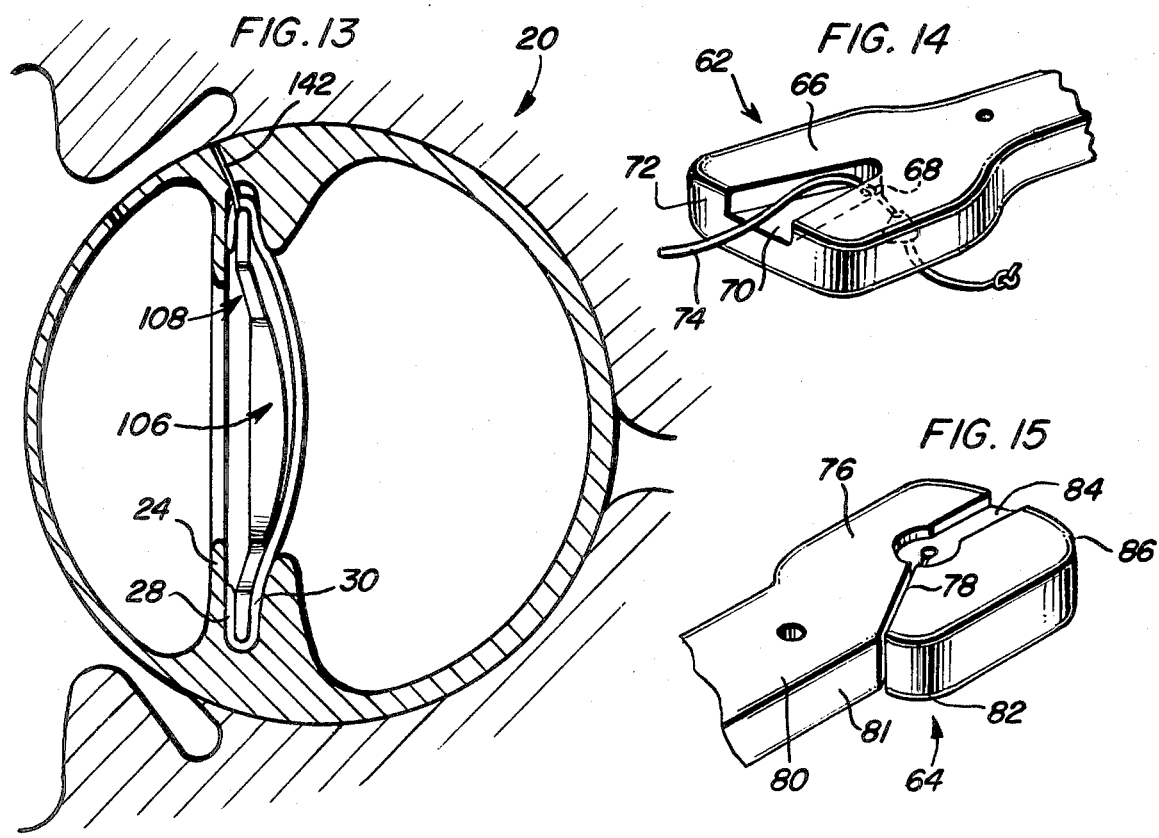

INTRAOCULAR LENSES

BACKGROUND OF THE INVENTION

Field of the Invention

This invention relates to improvements in intraocular lenses suitable for use as artificial lens implants and to a method for securing the lens within either of the anterior or posterior chamber of the human eye.

The natural crystalline lens in man is an optically clear organ situated behind the pupillary aperture of the eye. The function of this lens is to help form a sharp image on the retina to provide for acuity of vision. In certain circumstances opacity may develop in the lens, necessitating the surgical extraction of the natural lens from the eye. The condition of lens opacity is called cataract. The absence of the crystalline lens from the eye is known by the term aphakia. After the extraction of the lens, the eye is defective from an optical point of view due to the loss of diffraction of the lens, which should be corrected with optical aids. The optical correction of this connection is called aphakic correction.

The implantation of an artificial intraocular lens is a surgical technique which in recent years has come into increasing use for the correction of aphakia. It will be understood that with the implanting of an artificial intraocular lens in either of the anterior or posterior chambers of the human eye to replace the natural crystalline lens of the eye, severe demands are made on positioning and maintaining the artificial lens fixed within the desired eye chamber.

Accordingly, a vastly increasing number of designs of intraocular lenses are being made available in order to improve the ease at which surgical implantation of the lens can be performed and to provide more exact and assured fixation of the lens in the eye. Most of the available intraocular lenses include lobes or position fixation elements which are in the form of two or more loops. In some lenses, anteriorly as well as posteriorly mounted loops are provided. The fixation loops extend generally radially of the plano-convex lens body and are spaced from one another generally at opposite positions around the periphery of the lens body and are substantially disposed in a common plane with the plano-convex lens. Recently, the fixation elements for artificial lenses have been made unitary with the lens body such that they are not separately attached elements but are formed with the lens body by molding or machining or the like, a single block of any suitable physiologically inert and nontoxic synthetic resin such as are well known to the art, e.g. polymethylmethacrylate.

As stated above, lens implantations are not only extremely difficult and delicate operations, but the use of currently available intraocular lenses, even by a highly skilled surgeon, entails a number of disadvantages. One disadvantage is that available lenses are somewhat difficult to manipulate, given the relatively limited environment within which the surgical implantation is accomplished. As a result, improper fixation of the lens can easily occur, which often makes it necessary for the surgeon to go back into the eye within a few days after the initial implantation in order to correct the positioning error. Another disadvantage is that the lenses are often not provided with suture fixation capabilities. While some surgeons to not feel the necessity of suture fixation, there are times when suture fixation can greatly aid in the process of implanting the intraocular lens as well as provide assured fixation of the lens within the eye chamber. For example, dislocation of the implanted lens is averted, whether from side-to-side or down into the vitreous through ruptured zonules. With superior limb fixation, there is no propeller effect from lenses that may not be of the proper size. Further, during experiences of a traumatic iris prolapse superiorly which could be excised the lens will be securely held by a suture in spite of the absence of the iris at the superior position. Still another disadvantage of available lenses derives from the need to manipulate surgical instrumentation within the eye during implantation and positioning, requiring extremely delicate surgical techniques.

Typical of relatively recent intraocular lens structures which have been patented include U.S. Pat. Nos. 4,174,543, issued Nov. 20, 1979 to Kelman, which discloses an anterior chamber lens provided with four point position fixation formed substantially from a pair of laterally extending and deflectable fixation elements, no suture capacity being provided; 4,092,743, issued June 6, 1978, also to Kelman, which comprises an intraocular lens provided with two lateral position fixation elements, the dimensions as well as the structure of the fixation elements are such that the lens can be snaked through a corneo-scleral incision which can be made only slightly longer than the diameter of the lens body, the superior limb fixation element being provided with a suture hole; and 4,110,848, issued Sept. 5, 1978 to Jensen which discloses an intraocular lens for implantation into the posterior chamber of the eye in which the lower fixation loop has a notch which is disposed between the peripheral edge of the plano-convex lens body and the end portion of the loop so that a suture can temporarily secure the lens to the iris of the eye, the fixation loops are mechanically coupled to the peripheral edge of plano-convex lens and may be formed of the same material as the lens body.

SUMMARY OF THE INVENTION

In view of the foregoing factors and disadvantages of the intraocular lenses of the prior art, it is a primary object of the present invention to provide intraocular lenses for implantation into either the anterior or posterior chamber of the human eye in which implantation of the lenses can be accomplished easier and with more exact positioning and secured fixation than prior art lenses.

It is another object of the present invention to provide intraocular lenses designed for placement into either the anterior or posterior chamber of the human eye and which have the capacity to firmly hold a suture for permanent fixation of the lens in the respective eye chamber.

It is still another object of the present invention to provide intraocular lenses containing a novel fixation element so constructed that the lens will be easier to insert properly in position than heretofore known lens structures and to allow permanent fixation of the lens with a suture without the requirement of instrumentation contacting internal eye structure.

Still yet another object of the present invention is to provide an intraocular lens which includes a laterally extending superior fixation element which has a capacity to hold a suture for permanent fixation of the lens and is so constructed to enable easy manipulation and fixation of the lens to the sclera and, optionally, the iris.

Basically, the objectives of the present invention are achieved by two intraocular lens constructions, one for implantation into the anterior chamber and the other for implantation into the posterior chamber, both types of lens being characterized by a plano-convex lens body and two lens position fixation elements projecting from spaced, generally opposite peripheral regions of the lens body. One of these fixation elements, referred to throughout the remainder of the specification, as the superior limb due to the contact of the fixation element with the upper eye structure is of a novel construction enabling the intraocular lens to be permanently secured to the respective eye chamber and allows easy manipulation of the lens during implantation and fixation. The superior limb is contiguous with the plano-convex lens body and extends laterally from the peripheral edge of the lens body and terminates in a flattened and widened head portion which is provided with suture holding capability in the form of a suture hole or slit which extends from the point at which the superior limb begins to widen (proximal) substantially diagonally across the terminal head to about the center thereof. The upper flat surface of the terminal head includes a depression extending from the distal edge and encloses the suture hole or end of the suture holding slit placed near the center of the terminal head so as to provide a guide for the instrument used to thread the suture through the superior limb, the bottom surfaces of the flattened terminal head comprising a depressed area surrounding the suture hole or end of the slit to accommodate a knot which is placed at the end of the suture for permanent fixation of the lens to the respective chamber. The superior limb further contains a hole therethrough positioned substantially immediately preceding the flattened terminal head for the engagement of a Sinsky hook which is used to manipulate the lens through the corneo-scleral incision. The other fixation element or lower limb also projects laterally from the peripheral edge of the plano-convex lens body but varies in structure depending on whether the lens is to be placed in the anterior or posterior chamber, variations also occurring in the posterior chamber lens. Primarily, the lower limb fixation element comprises an elongated limb body spaced from the plano-convex lens body and which extends from an attachment stem contiguous with the lens body traversely at least partly following the arcuate periphery of the lens body or comprises open or enclosed loops spaced slightly from the lens by means of a lateral stem contiguous with the lens body.

Preferably, both the superior limb and a lower limb fixation elements are unitary with the lens body and are formed with the plano-convex lens body by molding or machining a single block of any suitable physiologically inert and non-toxic synthetic resin such as polymethylmethacrylate which has well known use in forming intraocular lenses. However, the fixation elements in particular, the lower limb, may be formed separate from the plano-convex lens body and attached thereto although the fixation element may be constituted by either the same or similar plastic forming the lens body.

The laterally projecting fixation elements may be coplanar with the plano edge of the plano-convex lens body or may be vaulted, e.g. slightly displaced from the plano edge of the lens body in a direction opposite the convex surface of the lens body.

These together with other objects and advantages which will become subsequently apparent reside in the details of construction and use as more fully hereinafter described and claimed, reference being had to the accompanying drawings forming a part hereof, wherein like numerals refer to like parts throughout.

BRIEF DESCRIPTION OF THE DRAWINGS

FIG. 1 is an illustration of a vertical section through a human eye and shows a lens structured according to the present invention implanted in the anterior chamber of the eye.

FIG. 2 is a plan view of an intraocular lens illustrating the slit type of suture holding capability of the superior limb.

FIG. 3 is a side view of the intraocular lens of FIG. 2 and illustrating vaulted fixation elements used for implanation in the anterior chamber of the eye.

FIG. 4 is a fragmentary enlarged vertical section of the human eye illustrating the placement of an anterior lens and illustrating the trabecular flap which is formed in the scleral bed for holding the suture.

FIG. 5 is a plan view of an intraocular lens equivalent to that of FIG. 2 but illustrating the hole type of suture holding capability of the superior limb, the lens being capable of implantation into the posterior chamber of the eye.

FIG. 6 is a side view of the posterior chamber lens of FIG. 5 in the vaulted form of the lens.

FIG. 7 is a side view of the posterior chamber lens of FIG. 5 illustrating the coplanar form of the lens.

FIG. 8 is a plan view of an alternative posterior chamber lens (slit type) containing a modified lower limb structure.

FIGS. 9 and 10 are side views of the posterior chamber lens of FIG. 8 in the vaulted and coplanar form, respectively.

FIG. 11 is a plan view of another posterior chamber lens (slit type), the lower limb being formed as an oblong loop attached to the plano-convex lens body.

FIG. 12 is a plan view of still another alternative posterior chamber lens (slit type) in which the lower limb is an oblong loop which is formed integrally with the plano-convex lens body.

FIG. 13 is a vertical section through the human eye showing implantation of an intraocular lens of the present invention in the posterior chamber.

FIG. 14 is a fragmentary perspective view illustrating the top surface of the suture hole type of superior limb.

FIG. 15 is a fragmentary perspective view illustrating the top surface of the slit type superior limb.

FIG. 16 is a fragmentary perspective view illustrating the bottom surface of the superior limb (slit type).

DETAILED DESCRIPTION OF THE INVENTION

Referring to FIG. 1, reference numeral 20 refers to the human eye in which portions of the eyeball structure which are not believed essential to the understanding of the invention have been omitted for the sake of clarity. Eyeball 20 includes cornea 22, iris 24 having a central opening or pupil 26, anterior capsule membrane 28, posterior capsule membrane 30 and a retina 32. The natural lens, which normally occupies the area between capsule membrane 30 and iris 24 has been omitted since the present invention deals with artificial substitutes for the natural lens.

An aqueous zone between cornea 22 and capsule membrane 30 is subdivided by iris 24 into an anterior chamber 34 and a posterior chamber 36. A scleral spur 38 is present in the anterior chamber 34 spaced from iris 24.

Intraocular artificial lens 42 is positioned in anterior chamber 34 and includes a plano-convex light focusing lens body 44 and a pair of oppositely lateral projecting fixation elements comprising superior limb fixation element 46 and lower limb fixation element 48. The terminal ends of fixation elements 46 and 48 lie behind the scleral spur 38. Intraocular lens 42 is placed within the anterior chamber 34 of eyeball 20 by making a corneal incision 50 and passing lens 42 therethrough.

FIGS. 2 and 3 illustrate the structure of intraocular lens 42 which is implanted within the anterior chamber 34 of eyeball 20. Fixation elements 46 and 48 are vaulted or in other words displaced from the longitudinal plane of plano surface 45 of lens body 44.

Superior limb 46 comprises a narrow laterally extending stem portion 52 contiguous with lens body 44 and formed integrally therewith. The end of superior limb 46 comprises a flattened and widened terminal head 54 which is provided with suture holding capability to permanently and securely fix lens 42 in the anterior chamber 34. Superior limb 46 as illustrated in FIG. 2 is a form of the invention labelled the slit type superior limb in view of the suture holding slit 56 which extends from proximal peripheral edge 58 of terminal head 54 and extends diagonally across the face of terminal head 54 and ends roughly in the center thereof. Formed on the upper flattened surface of terminal head 54 and extending from the distal peripheral edge of terminal head 54 to and enclosing the terminal end of slit 56 is depression 60 which aids in guiding the instrument used to thread the suture through slit 56. The fixation suture lies in depression 60.

FIGS. 14 and 15 illustrate the alternative suture holding capabilities of the superior limb and which can be referred to as the hole type superior limb indicated by reference numeral 62 in FIG. 14 and the slit type superior limb 64 illustrated in FIG. 15. Both Figures illustrate the upper surface of the respective superior limbs. Referring to FIG. 14, superior limb 62 includes widened flattened terminal head 66 which is provided with a suture hole 68 placed at the approximate center of head 66. A V-shaped depression 70 in the upper surface of terminal head 66 and extending from the peripheral distal edge 72 of head 66 and engulfing suture hole 68 is provided so as to aid in guiding the surgical instrument which threads suture 74 through suture hole 68. The slit type superior limb 64 illustrated in FIG. 15 incorporates an alternative suture holding capability to superior limb 62 but, nevertheless, it is of the same general concept. Accordingly, superior limb 64 includes a widened flatten terminal head 76 which has passing fully through the depth thereof an elongated suture holding slit 78 which extends transversely from the proximal edge of widened head 76 diagonally toward the approximate center of flattened terminal head 76. The point at which slit 78 begins is preferably at the point of the intersection of the peripheral edge 81 of elongated stem 80 of superior limb 64 and edge 82 which extends transversely from the longitudinal extent of edge 81 and forms the proximal peripheral edge of terminal head 76. Upon the upper surface of terminal head 76 is formed depression 84 which extends from distal edge 86 of terminal head 76 and engulfs the terminal end portion of suture holding slit 78 for the purpose of accurately and easily guiding the instrument which is used to thread the suture through slit 78. The bottom surface of the terminal head of each of the superior limbs is structured so as to accommodate a knot which is placed at the end of the suture during implantation and fixation of the limbs in the respective eye chamber. Referring to FIG. 16, the bottom surface of the flattened head 76 of a slit type superior limb 64 is illustrated in which surface a second depression 88 is formed surrounding the terminal portion of suture holding slit 78. The bottom surface of a hole type superior limb would also include a depression, one that surrounds the suture passing fully through the depth of the terminal head portion.

Referring again to FIGS. 2 and 3, lower fixation element 48 includes a laterally projecting stem 90 contiguous with and preferably integrally molded or machined with the plano-convex lens body 44. A leg portion 92 extends from the distal end of stem 90 and extends transversely thereto following substantially the arcuate periphery of lens body 44. The length of leg 92 is approximately one-third of the circumference of lens body 44, length of stem 90 obviously determining the spacing between lens body 44 and leg 92, the spacing being provided so that fixation element 48 can lie behind scleral spur 38 and in front of iris 24. Stem 90 and leg 92 are of a one-piece construction preferably integrally molded or machined out of the same block of material forming lens body 44. Apertures 94 and 96 are placed in the superior limb 46 and lower limb 48, respectively, for engagement by a Sinsky hook used to manipulate the intraocular lens during passage through the corneal incision and for implantation into the desired chamber of the eye. Aperture 94 is preferably positioned immediately preceding proximal edge 58 of flattened head 54 and is positioned approximately at the transverse center of stem 52. Aperture 96 as shown is positioned proximal to stem 90 in leg 92.

Fixation elements 46 and 48 in anterior chamber lens 42 are vaulted or in a non-coplanar relationship with plano surface 45 of lens 44. Accordingly, stems 52 and 90 are angled slightly away from the vertical plane passing through plano-convex lens body 44 in a direction opposite that of the convex surface of lens body 44. Terminal head 54 and leg 92 are angled from stem 52 and 90, respectively, and lie in a substantially vertical plane parallel to the vertical plane passing through lens body 44.

It will be understood, of course, that the precise dimensions of anterior chamber intraocular lens 42 are in and of themselves not critical aspects of the present invention, since the physiological make-up of the eye of different human beings may well dictate the choice of lenses of slightly different dimensional characteristics. Merely by way of example, however, the following dimensions are presented to indicate a representative lens 42 for implantation into anterior chamber 34. The diameter of plano-convex lens body 44 may be about 4 to preferably about 6 mm with a typical maximum thickness of about 0.4 mm. The overall length of intraocular lens 42 may range between about 11 and about 14.5 mm, each fixation element 46 and 48 extends approximately 2–2.5 mm from lens body 44, terminal head 54 having a length of approximately 1.6 mm and leg 92 having a width of about 1.0 mm and is spaced from lens body 44 by about 1.0 mm. Stems 52 and 90 extend from the peripheral edge of plano-convex lens body 44 by approximately 0.5 to about 1.0 mm. The width of stem 52 may be about 1.5 mm while terminal head 54 has a width of approximately 2 mm. The vault angle of stems 52 and 90 from the vertical plane passing through plano surface 45 of lens body 44 is approximately 7.5°. The width of depressions 70 or 84 (FIGS. 14 and 15) must be large enough to accommodate a closed forceps allowing the suture to be easily and accurately guided to the respective suture holding structures engulfed by the depressions on the upper surface of either the hole type or slit type superior limb.

FIGS. 5-7 illustrate an intraocular lens generally indicated by reference numeral 98 and which can be implanted in the posterior chamber 36 of the eye as shown in FIG. 13. Intraocular lens 98 is shown with a superior limb 100 of the hole type. It will, of course, be understood that intraocular lens 98 could include the slit type of superior limb. The configuration of intraocular lens 98 is substantially equivalent to intraocular lens 42 which can be implanted in anterior chamber 34 of eye 20, intraocular lens 98 comprising plano-convex lens body 102, superior limb 100 and lower limb 104 for fixation of lens 98 within the posterior chamber 36 of eye 20. The superior limb structure which is useful in the anterior chamber lens 42 is equivalent to the superior limb which is attached and forms the superior fixation element of posterior intraocular lens 98. Similarly, lower limb 104 of lens 98 is equivalent to lower limb 48 of anterior chamber lens 42. One important difference between posterior chamber lens 98 and anterior lens 42 relates to the orientation of fixation members 100 and 104. in anterior chamber lens 42, the superior and lower limbs must be vaulted whereas in posterior chamber intraocular lens 98 superior limb 100 and lower limb 104 can be vaulted as illustrated in FIG. 6 or coplanar with the vertical plane of the plano surface of lens body 102 as illustrated in FIG. 7. In positioning posterior chamber intraocular lens 98 and the alternative posterior chamber lenses illustrated in FIGS. 8-12, the convex surface of the lens body faces the posterior of the human eye. As shown in FIG. 13, posterior chamber intraocular lens 106 is positioned within posterior chamber 36 such that the lower limb is positioned within the capsule bag formed by anterior capsule membrane 28 and posterior capsule membrane 30. The alternative posterior chamber lenses may have the lower fixation element either in the capsular bag or the ciliary sulcus. Superior limb 108 can be fixed by a suture to the sclera or iris 24. It is possible that the suture fixation may be omitted by choice of the surgeon.

The dimensions of posterior chamber intraocular lens 98 are equivalent to the dimensions set forth for intraocular lens 42. Of course, there may be slight variances due to structural and dimensional differences between the anterior and posterior chambers.

FIGS. 8-10 illustrate an alternative form of posterior chamber intraocular lens and is generally indicated by reference numeral 110 and may include either the slit or hole type superior limb 112 and lower fixation element 114 which can be an integral of plano-convex lens body 116 or configured separately and grafted to the lens body. The only difference between the various posterior chamber intraocular lenses illustrated in FIGS. 5, 8, 11 and 12 are in the lower fixation elements, the superior limb structures for each of these intraocular lenses being equivalent. Lower fixation element 114 of posterior chamber intraocular lens 110 can be defined as an unclosed loop in which a loop stem 118 projects laterally from the peripheral edge of lens body 116 and then develops into a transverse oblong loop structure which transverses the longitudinal plane passing through lens body 116 and laterally projecting superior limb 112. Intraocular lens 110 can be formed in both the vaulted or coplanar forms as illustrated in FIGS. 9 and 10, respectively. In the vaulted form, stem 118 and stem 120 of superior limb 112 are displaced approximately 5°-7.5° from the plano surface 122 of lens body 116. Posterior chamber intraocular lens 110 has an overall length of apoproximately 12-12.5 mm for human eyes with corneas greater than 12 mm. The transverse length of lower unclosed loop 114 may be from about 7-8 mm. The remaining dimensions are substantially equivalent to the dimensions of anterior chamber intraocular lens 42. Aperture 124 placed at the outer periphery of lens body 116 is large enough to accommodate a Sinsky hook.

FIGS. 11 and 12 illustrate still further alternative posterior chamber intraocular lenses 126 and 128, respectively. The plano-convex lens body 130 and 132 of intraocular lenses 126 and 128, respectively, are equivalent to the respective structures in lenses 98 and 110 as well as are superior limbs 134 and 136 of the respective posterior chamber lenses. Again, it is to be understood that the slit type of superior limb illustrated in each of intraocular lenses 126 and 128 can be replaced with the hole type of superior limb illustrated in FIG. 14. The difference between intraocular lenses 126 and 128 is in the lower fixation elements 138 and 140, in which lower closed loop 138 is formed separately and grafted onto lens body 130 while lower closed loop 140 is formed integrally with lens body 132. Preferably, the material which forms each of the lenses of the present invention is polymethylmethacrylate although other physiologically inert synthetic resins can be utilized. Both intraocular lenses 126 and 128 can be vaulted or coplanar and if in the vaulted form, the displacement of the fixation elements being approximately 5°-7.5° from the vertical plane passing longitudinally through the lens. Over-all the dimensions of posterior chamber intraocular lenses 126 and 128 are similar or equivalent to intraocular lens 110 including closed loops 138 and 140 which are also approximately 7.0 to 8.0 mm in length measured transversely across the vertical plane passing through the lens body and the superior limb.

The manner in which the individual intraocular lenses are placed in their respective anterior or posterior chambers of a human eye can be described with respect to FIGS. 1, 4 and 13, however, it will of course be understood that the present invention does not relate to a surgical method and the description to follow is one that only briefly describes the implantation of the intraocular lens and the permanent fixation or the lens into the respective eye chamber. Certain advantages which are derived from the structure of the intraocular lenses of the present invention will be clearly seen by the brief description of implantation and fixation. Accordingly, after the patient has been properly prepared and anesthetized, a corneo-scleral incision 50 is made in eyeball 20 near the upper front region thereof. A triangular partial thickness scleral flap is prepared in the 12 o'clock position relative to incision 50 and is provided with a 2.5 mm base approximately 1 mm superior to corneo-scleral incision 50. It is within the scleral bed exposed by lifting the flap that the suture needle emerges and suture 142 is tied upon itself after the intraocular lens has been passed through the incision and properly positioned in the respective eye chamber. The sharp end of the suture is rounded by cautery heat and the partial thickness sclereal flap is then replaced over the scleral bed thus covering the cut end of the suture. The partial thickness scleral flap is used when desired with either the anterior chamber or posterior chamber lenses.

In posterior chamber fixation, the suture is brought behind iris 24 (FIG. 13) at the 12 o'clock position and out of the base of the trabecular flap after the corneal incision has been completed. The suture can be used as an iris retractor to aid in the expression of the nucleus and again the suture can be used to retract the iris during irrigation and aspiration of remaining cortical material. At this point the suture 142 can be threaded through the suture hole formed in the hole type superior limb and the end of the suture heated to form a small ball or the suture can be slipped into the slit of the slit type superior limb so that the ball of the suture is caught in the depressed area on the bottom surface of the superior limb indicated by reference numeral 88 in FIG. 16, the ball at the end of the suture serving as traction and fixation for the posterior chamber intraocular lens. Furthermore, a ball can be formed on the other end of the suture at the base of the trabecular flap so that a small portion of the suture is left to hold the lens and fixate the lens in the sclera in the shape of a dumbell. The suture can again be used for the third time to retract the iris at the moment of lens insertion. The 0.3 mm aperture in the superior limb stem is engaged by a Sinsky hook and the lens maneuvered under the iris while the iris is retracted by the suture. In this manner, little instrumentation has been placed within the eye contrary to what is often necessary with prior art lenses during their placement in the posterior chamber and subsequent horizontal positioning or twirling. The unique superior limb structure of the present invention allows the suture to be easily guided into the suture hole or slit and be held in position by forming the ball or knot at the end of the suture which is held on the opposite side of the limb from which it was threaded.

Superior limb fixation for an anterior chamber intraocular lens is relative easy in that iris 24 is not touched as the suture is simply brought out under the sclera lip into partial thickness scleral flap base 144 anterior to iris 24. However, the advantage of this fixation for the anterior chamber lens is that fixation in this manner prevents propelling of the lens into peripheral iridectomies and provides support so that the entire weight of the anterior chamber lens is not exclusively on the inferior portion of the eyeball.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. In an intraocular lens implant having a lens body and at least two fixation elements connected to the lens body in circumferentially spaced relation to each other, the improvement residing in a configuration of one of the fixation elements enhancing in-situ suturing of the implant, including a stem portion connected to the lens body and a terminal head portion connected to the stem portion in radially spaced relation to the lens body, said terminal head portion having a radially inner edge extending laterally from the stem portion and a radially outer distal edge spaced from the inner edge, the terminal head portion being formed with a suture holding aperture spaced between the edges and suture guiding means extending between the aperture and at least one of the edges, said guiding means including a slit extending from the aperture to the inner edge substantially at the stem portion.

2. The improvement as defined in claim 1 wherein the guiding means further includes a depression in the head portion extending from the aperture to the distal edge.

3. In an intraocular lens implant having a lens body and at least two fixation elements connected to the lens body in circumferentially spaced relation to each other, the improvement residing in a configuration of one of the fixation elements enhancing in-situ suturing of the implant, including a stem portion connected to the lens body and a terminal head portion connected to the stem portion in radially spaced relation to the lens body, said terminal head portion having a radially inner edge extending laterally from the stem portion and a radially outer distal edge spaced from the inner edge, the terminal head portion being formed with a suture holding aperture spaced between the edges and suture guiding means extending between the aperture and at least one of the edges, the guiding means including a depression in the head portion extending from the aperture to the distal edge.

4. The improvement as defined in claim 3 wherein the depression diverges from the aperture toward the distal edge.

5. An intraocular lens suitable for use as an artificial lens implant comprising: a light-focusing plano-convex lens body, a superior fixation element and at least one lower fixation element, said superior fixation element extending laterally from a first region on the periphery of said lens body and comprising means to hold a suture for fixation of said lens within the eye and further including a means to accurately guide a suture into said suture holding means, said lower fixation element projecting laterally from a second region of the periphery of said lens body spaced and generally opposite said first region, said superior fixation element having an upper surface, said suture holding means including aperture means passing entirely through the depth of said superior fixation element, said suture guide means being provided on said upper surface, said superior fixation element including a peripheral edge, said aperture means comprising a slit extending from a proximal region of said peripheral edge relative to said lens body outwardly toward a distal end and centrally of said superior fixation element, said superior fixation element further including a widened and flattened terminal head portion, said peripheral edge of said superior fixation element including a longitudinal peripheral edge and a transverse peripheral edge of said head portion proximal with respect to said lens body, said slit extending from the intersection of said longitudinal peripheral edge and said transverse peripheral edge to substantially centrally of said terminal head portion.

* * * * *